(12) United States Patent
Liu et al.

(10) Patent No.: US 7,242,010 B2
(45) Date of Patent: Jul. 10, 2007

(54) GASE CRYSTALS FOR BROADBAND TERAHERTZ WAVE DETECTION

(75) Inventors: Kai Liu, Troy, NY (US); Xi-Cheng Zhang, Melrose, NY (US); Jingzhou Xu, Troy, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 84 days.

(21) Appl. No.: 11/086,623

(22) Filed: Mar. 22, 2005

(65) Prior Publication Data

US 2006/0214114 A1  Sep. 28, 2006

(51) Int. Cl.
*G01J 5/58* (2006.01)

(52) U.S. Cl. .................................. 250/474.1
(58) Field of Classification Search ............. 250/474.1
See application file for complete search history.

(56) References Cited

FOREIGN PATENT DOCUMENTS

JP          2005037213 A  *  2/2005

OTHER PUBLICATIONS

Kubler et al., Ultrabroadband detection of multi-terahertz field transients with GaSe electro-optic sensors: Approaching the near infrared, *Applied Physics Letters*, vol. 85, No. 16, Oct. 18, 2004, pp. 3360-3362.
Huber et al., Generation and field-resolved detection of femtosecond electromagnetic pulses tunable up to 41 THz, *Applied Physics Letters*, vol. 76, No. 22, May 29, 2000, pp. 3191-3193.
Tanabe et al., Characteristics of terahertz-wave generation from GaSe crystals, *Journal of Physics D: Applied Physics*, vol. 37, 2004, pp. 155-158.
Sinyukov et al., Generation and detection of terahertz radiation with multilayered electro-optic polymer films, *Optics Letters*, vol. 27, No. 1, Jan. 1, 2002, pp. 55-57.
Kai Liu et al., "GaSe crystals for broadband terahertz wave detection", Applied Physics Letters, AIP, American Institute of Physics, vol. 85, No. 6, Aug. 9, 2004, pp. 863-865.
Bradley Ferguson et al., "Materials for terahertz science and technology", Nature Materials, vol. 1, Sep. 2002, pp. 26-33.
International Search Report for PCT Application No. PCT/US2006/008370 mailed Jul. 19, 2006 not a publication.

(Continued)

*Primary Examiner*—Constantine Hannaher
(74) *Attorney, Agent, or Firm*—RatnerPrestia

(57) ABSTRACT

A broad bandwidth detector to measure intensity information of terahertz (THz) frequency pulses. The detector includes: coupling optics coupled to a coherent optical source; a GaSe substrate aligned such that the probe beam path intersects a first surface at a phase-matching angle; a polarization detector aligned in the probe beam path; and calculation means coupled to the polarization detector. The coupling optics direct the probe optical beam along a beam path that is substantially collinear with the pulse beam path of the THz frequency pulses. The polarization of the probe optical beam is varied based on interactions between the probe optical beam and the THz frequency pulses within the GaSe substrate. The polarization detector detects the varied polarization of the probe optical beam. The calculation means determine the intensity information of the THz frequency pulses based on the detected probe polarization of the probe optical beam.

23 Claims, 5 Drawing Sheets

OTHER PUBLICATIONS

K. H. Yang, P. L. Richards, and Y. R. Shen; Generation of Far-Infrared Radiation by Picosecond Light Pulses in $LInBO_3$; Appl. Phys. Lett. 19, 320 (1971).

Q. Wu and X.-C. Zhang; Free-Space Electro-Optics Sampling of Mid-Infrared Pulses; Appl. Phys. Lett. 71 (10) 1285 (1997).

A. Nahata, A. S. Weling, and T. F. Heinz; a Wideband Coherent Terahertz Spectroscopy System Using Optical Rectification and Electro-Optic Sampling; Appl. Phys. Lett. 69, 2321 (1996).

P. U. Jepsen, C. Winnewisser, M. Schall, V. Schyia, S. R. Keiding, H. Helm; Detection of THz Pulses by Phase Retardation in Lithium Tantalite; Phys. Rev. E, 53, 3052 (1996).

W. Wu and X.-C Zhang; Free-Space Electro-Optic Sampling of Terahertz Beams; Appl. Phys. Letter 67 (24), Dec. 11, 1995. pp. 3523-3525.

W. Wu and X.-C Zhang; 7 Terahertz Broadband GaP Electro-Optic Sensor; Appl. Phys Letter 70 (14); Apr. 7, 1997. pp. 1784-1786.

P.Y. Han and X.-C. Zhang; Coherent, Broadband Midinfrared Terahertz Beam Sensors; Appl Phys. Letter vol. 73, No. 21; Nov. 23, 1998. pp. 3049-3051.

P.Y. Han and M. Tani, F. Pan and X.C. Zhang; Use of the Organic Crystal Dast for Terahertz Beam Applications; Optics Letters, vol. 25, No. 9; May 1, 2000. pp. 675-677.

Ajay Nahata, David H. Auston ,Tony F. Heinz and Chegjiu Wu; Coherent Detection of Freely Propagating Terahertz Radiation by Electro-Optic Sampling; Appl. Physics Letter 68 (2), Jan. 8, 1996. pp. 150-152.

A. M. Sinyukov, and L. M. Hayden; Generation and Detection of Terahertz Radiation With Multilayered Electro-Optic Polymer Films; Opt. Lett. 27, 55 (2002).

S. Kono, M. Tani, and K. Sakai; Coherent Detection of Mid-Infrared Radiation up to 60 THz With an LT-GaAs Photoconductive Antenna; IEEE Proc-Optele. 149, 105 (2002).

V. G. Dmitriev, G. G. Gurzadyhan, and D. N. Nikogosyan; The Springer Handbook of Nonlinear Optical Crystals; 166-169 (1999). cover and pp. 166-169.

Reimann, R. P. Smith, A. M. Weiner, T. Elsaesser, and M. Woerner; Direct Field-Resolved Detection of Terahertz Transients With Amplitudes of Megavolts Per Centimeter; Opt. Lett. 28, 471 (2003).

* cited by examiner

GASE CRYSTALS FOR BROADBAND TERAHERTZ WAVE DETECTION

FIELD OF THE INVENTION

The present invention relates generally to terahertz frequency wave detectors using GaSe crystals. More particularly, broad bandwidth GaSe terahertz frequency wave detectors for sub-picosecond terahertz frequency pulses.

BACKGROUND OF THE INVENTION

One method reported for the generation and detection of broadband THz radiation utilizes nonlinear optical effects, such as second order nonlinearity, optical rectification (K. H. Yang, P. L. Richards, and Y. R. Shen, Appl. Phys. Lett. 19, 320 (1971)), and electro-optical sampling (Q. Wu and X.-C. Zhang, Appl. Phys. Lett. 67, 3523 (1995), A. Nahata, A. S. Weling, and T. F. Heinz, Appl. Phys. Lett. 69, 2321 (1996), and P. U. Jepsen, C. Winnewisser, M. Schall, V. Schyia, S. R. Keiding, H. Helm, Phys. Rev. E, 53, 3052 (1996)).

Multiple broadband coherent generation and detection techniques have been demonstrated which use inorganic crystals, such as GaP (Q. Wu and X.-C. Zhang, Appl. Phys. Lett. 70, 1784 (1997)) and ZnTe crystals (Q. Wu and X.-C. Zhang, Appl. Phys. Lett. 71, 1285 (1997) and P. Y. Han, and X.-C. Zhang, Appl. Phys. Lett. 73, 3049 (1998)), the organic material DAST (P. Y. Han, M. Tani, F. Pan, and X.-C. Zhang, Opt. Lett. 25, 675 (2000)), or electro-optic polymers (A. Nahata, D. H. Auston, T. F. Heinz, and C. Wu, Appl. Phys. Lett. 68, 150 (1995) and A. M. Sinyukov, and L. M. Hayden, Opt. Lett. 27, 55 (2002)).

One alternative method uses a photoconductive antenna. The detection of broadband THz waves up to 60 THz was reported using a low-temperature-grown GaSa photoconductive antenna (S. Kono, M. Tani, and K. Sakai, IEEE Proc-Optele. 149, 105 (2002)).

The Handbook of Nonlinear Optical Crystals, (V. G. Dmitriev, G. G. Gurzadyhan, and D. N. Nikogosyan, Springer, 166-169 (1999)) describes GaSe as a nonlinear optical (NLO) crystal with layered hexagonal structure in a $\bar{6}2m$ point group. This crystal has a large electro-optic coefficient, high damage threshold, suitable transparent range, and a low absorption coefficient. GaSe is also a negative uniaxial crystal, with type-I phase matching in electro-optical sampling. Due to the large nonlinear optical coefficient ($d_{22}=54$ pm/V) and birefringence properties, GaSe is used in the generation of broadband mid-infrared electromagnetic waves. Recently, collinear difference-frequency generation with a nanosecond pulse laser (W. Shi, Y. J. Ding, N. Fernelius, and K. Vodopyanov, Opt. Lett. 27, 1454 (2002)), phase-matched optical rectification with a Ti:Sapphire laser (R. Huber, A. Brodschelm, F. Tauser, and A. Leitenstorfer, Appl. Phys. Lett. 76, 3191 (2000)), and field amplitudes greater than MV/cm in GaSe were reported (K. Reimann, R. P. Smith, A. M. Weiner, T. Elsaesser, and M. Woerner, Opt. Lett. 28, 471 (2003)). However, this crystal has not been explored in the context of broadband detection.

SUMMARY OF THE INVENTION

An exemplary embodiment of the present invention is a broad bandwidth detector for use with a coherent optical source to measure intensity information of terahertz (THz) frequency pulses having a THz pulse period. Each THz pulse has a THz pulse width. The broad bandwidth detector includes: coupling optics optically coupled to the coherent optical source; a GaSe substrate aligned such that the probe beam path intersects a first surface at a phase-matching angle; a polarization detector aligned in the probe beam path; and calculation means electrically coupled to the polarization detector. The GaSe substrate has a second surface substantially parallel to the first surface. The coupling optics direct the probe optical beam produced by the coherent optical source along a probe beam path that is substantially collinear with the pulse beam path of the THz frequency pulses. The probe polarization of the probe optical beam is varied based on interactions between the probe optical beam and the THz frequency pulses within the GaSe substrate. The polarization detector detects the varied probe polarization of the probe optical beam. The calculation means determine the intensity information of the THz frequency pulses based on the detected probe polarization of the probe optical beam.

It is to be understood that both the foregoing general description and the following detailed description are exemplary, but are not restrictive, of the invention.

BRIEF DESCRIPTION OF THE DRAWING

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures.

DETAILED DESCRIPTION OF THE INVENTION

One exemplary embodiment of the present invention uses a GaSe crystal in a system to perform broadband detection of terahertz (THz) frequency radiation. The central frequency, and spectral response, of the detector is tunable and the amplitude measured with an exemplary detector system including a GaSe crystal may exceed that detected by a ZnTe crystal based system with comparable detection bandwidth. The exemplary detection system is particularly well suited to detect time-domain waveforms and/order frequency-domain spectra of short duration (<1ps) THz frequency pulses.

Figure 1:
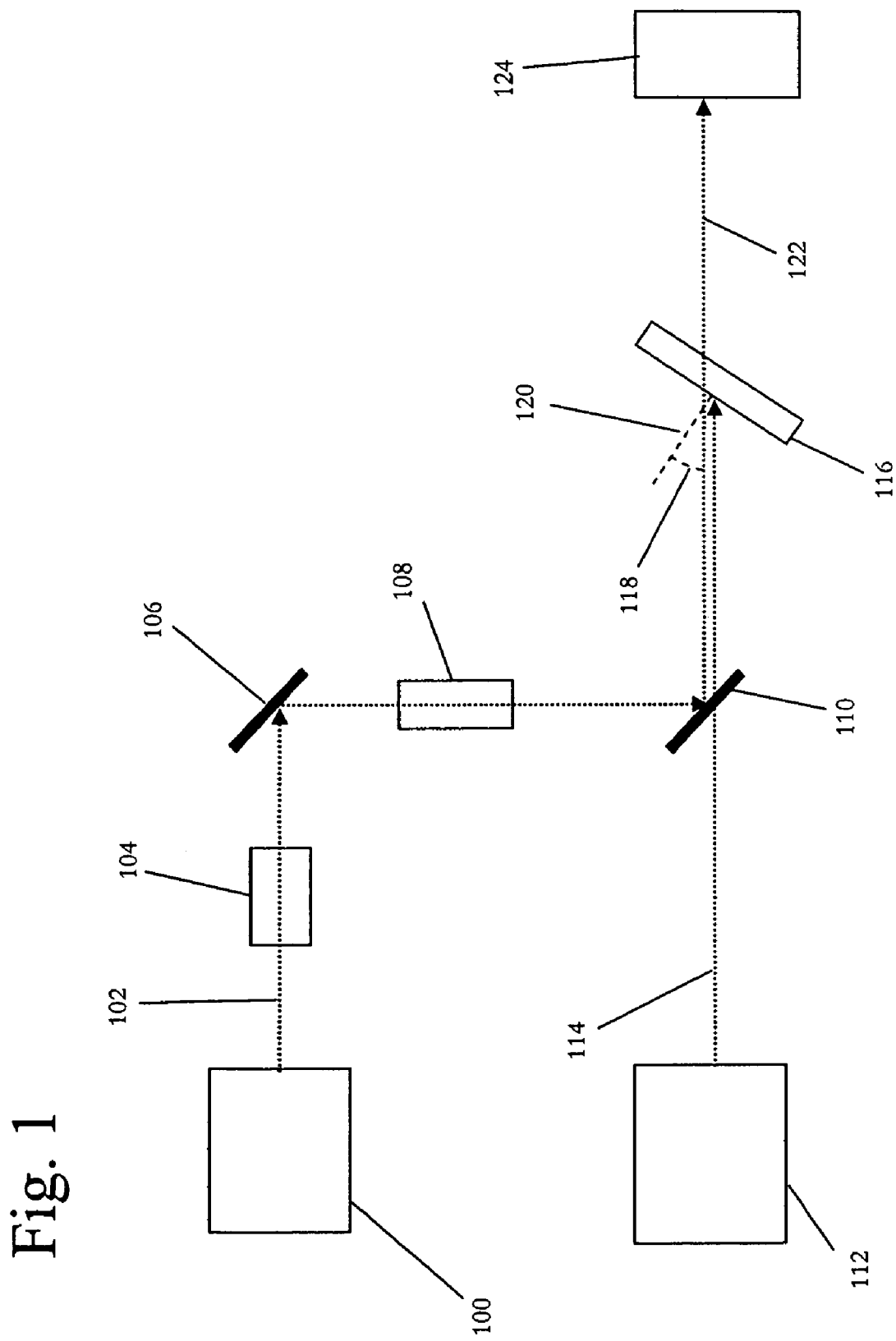
FIG. 1 is a schematic block diagram illustrating an exemplary GaSe terahertz frequency wave detector according to the present invention.

FIG. 1 illustrates an exemplary broad bandwidth detector that may be used to measure intensity information of THz frequency pulses.

The THz pulses to be detected are produced by THz pulse generator 112 and directed along pulse beam path 114. THz pulse generator 112 may use a number of methods such as optical rectification, collinear difference-frequency generation with a pulse laser, and electro-optical sampling may be used to generate THz frequency pulses. These pulses may desirably be produced with a constant pulse period. THz pulses generated by these exemplary techniques may have extremely short pulse widths, on the order of tens of femtosecond and, thus, may include only a few cycles of the THz frequency. Such THz pulses necessarily have broad bandwidths. Because of the difficulties associated with directly detecting these THz frequency pulses, the exemplary broad bandwidth detector of FIG. 1 detects changes in the polarization of a probe optical beam caused by nonlinear electro-optical coupling between the probe optical beam and the THz pulses within a GaSe crystal substrate.

The exemplary broad bandwidth detector of FIG. 1 includes coherent optical source 100 to produce the probe optical beam which propagates along probe beam path 102. The probe optical beam is generated with a known probe polarization, desirably a linear polarization. The probe optical beam has a probe peak wavelength which may be readily detected by polarization detector 124, desirably $\leq 1$ µm.

In one exemplary embodiment, the coherent optical source is a pulsed coherent optical source and the probe optical beam includes a series of probe pulses, which may be synchronized to the series of THz pulses. As described in the experimental example below, the probe pulses may be split from ultrafast pulses used to generate the THz pulses in THz pulse generator 112, in which case the probe pulse may have pulse width less than those of the THz pulses. One exemplary coherent optical source is a Ti:Sapphire ultrafast laser, which may produce probe pulses with pulse widths less than or equal to about 100 fs. Optical delay line 104 may be used to assist in synchronizing the probe pulses and the THz pulses. It is noted that although optical delay line 104 is shown to be aligned in probe beam path 102 to delay the probe pulses in FIG. 1, it may alternatively be aligned in THz beam path 114 to delay the THz frequency pulses.

Coupling optics are desirably used to direct the probe optical beam along probe beam path 102, such that the probe beam is substantially collinear with pulse beam path 114 of the THz frequency pulses when the two beam paths enter the front surface of GaSe substrate 116. These coupling optics may include mirror 106 and dichroic mirror 110. Dichroic mirror 110 may desirably be a multilayer dielectric mirror designed to be highly reflective at the peak wavelength of the probe optical beam and highly transmissive at the peak wavelength of the THz pulses.

Figure 2:
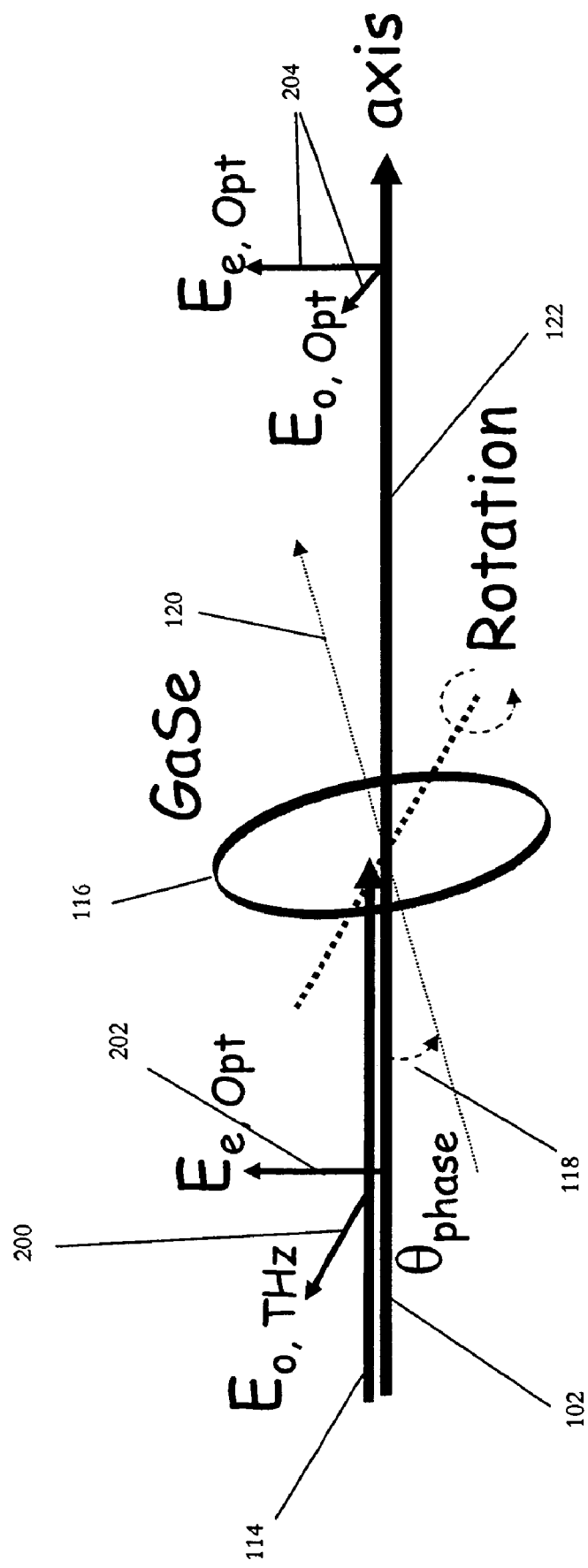
FIG. 2 is a schematic block diagram illustrating electro-optical effects on the polarization of an exemplary probe beam in an exemplary GaSe substrate.

GaSe substrate 116 has a front surface and a back surface that are substantially parallel and separated by an interaction thickness. The aligned probe optical beam and the THz pulses intersect the front surface of GaSe substrate 116 at phase-matching angle 118 (measured between probe beam path 102 and front surface normal 120). Desirably, the probe optical beam and THz pulses interact within GaSe substrate 116 as illustrated in the exemplary diagram of FIG. 2. This exemplary diagram illustrates how ordinary polarization 200 of the THz frequency radiation may interact with extraordinary polarization 202 of the probe optical beam within GaSe substrate 116, resulting in varying probe polarization 204. Varying probe polarization 204 desirably varies with the electric field of the THz pulse in a calculable manner. The resulting altered probe beam propagates along probe beam path 122.

Polarization detector 124 aligned in probe beam path 122 to detect the varying probe polarization of the probe optical beam. Desirably, polarization detector 124 may include a polarization means to separate one polarization component from the polarization varying probe optical beam and a high speed detector to measure the intensity of the separated polarization component. Alternately, the intensities of two orthogonal polarization components may be measured simultaneously. The intensity values correspond to the varying probe polarization. A signal representing the measured intensity value(s) may then be analyzed by calculation means (not shown) to determine the desired intensity information of the THz frequency pulses based on the detected probe polarization of the probe optical beam. These calculation means may include special purpose circuitry, an ASIC, a digital signal processor, and/or a general purpose computer.

Figure 3:
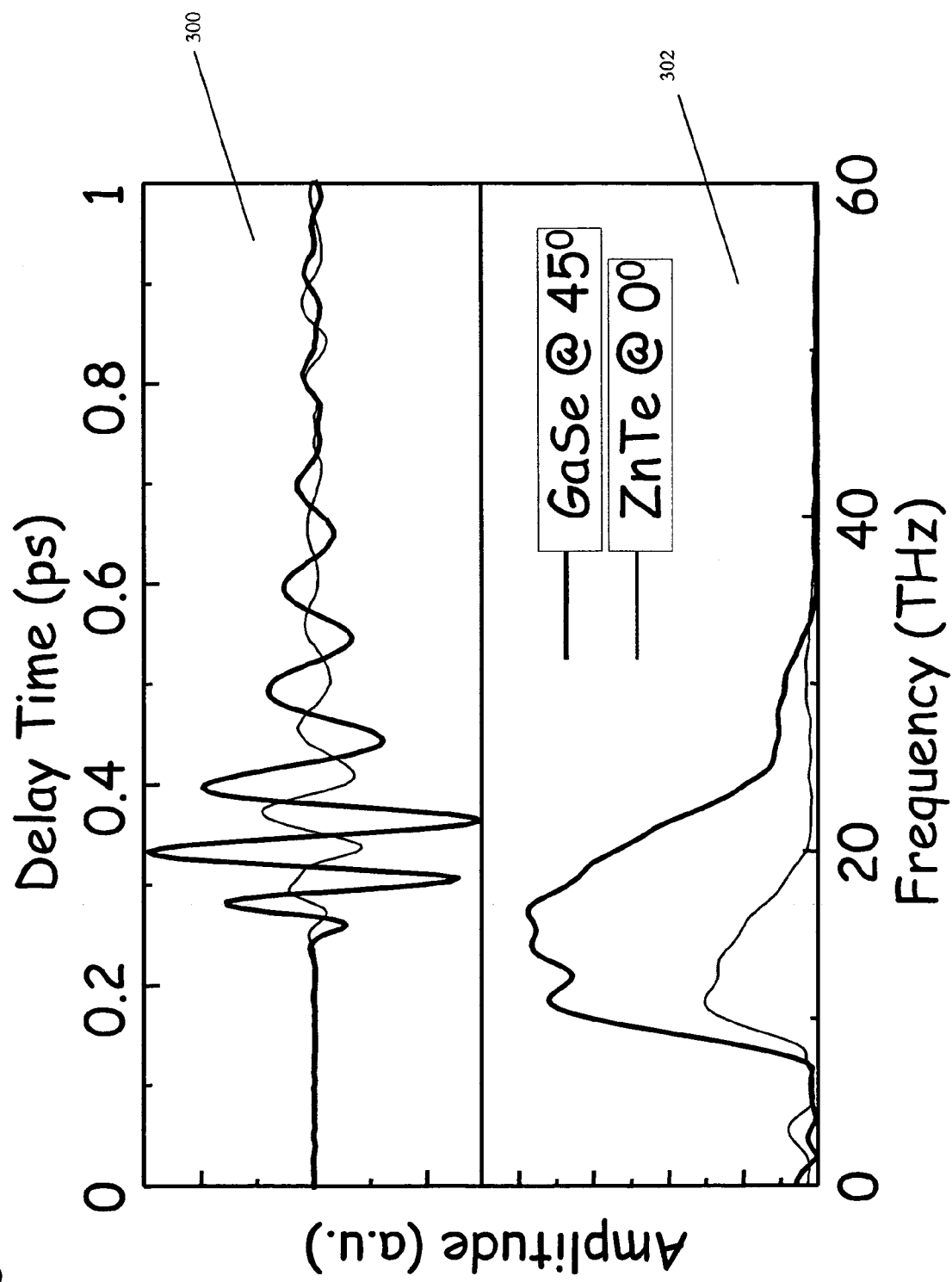
FIG. 3 is a graph illustrating exemplary intensity information measured by an exemplary GaSe terahertz frequency wave detector according to the present invention and an exemplary ZnTe terahertz frequency wave detector.
Figure 4A:
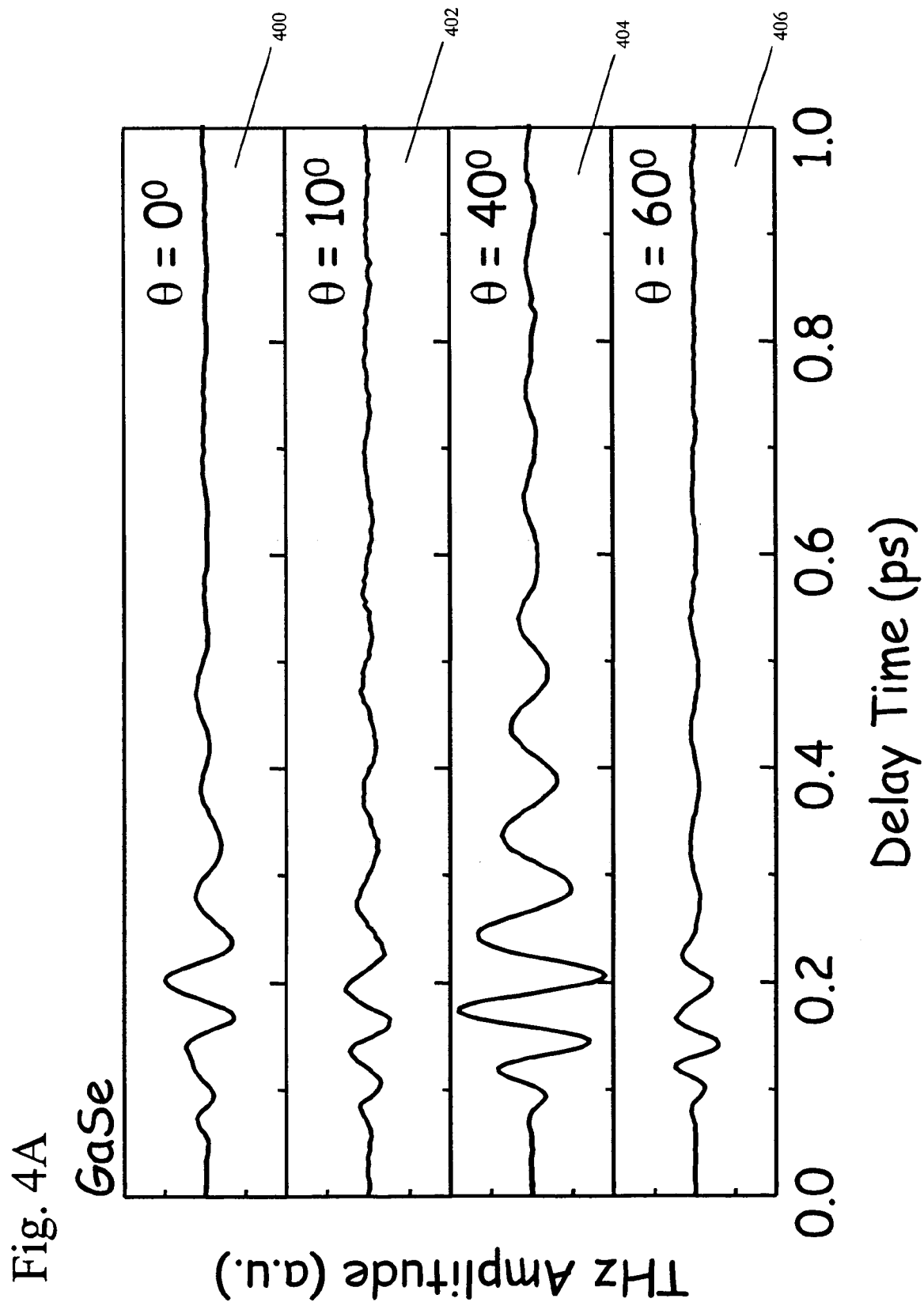
FIG. 4A is a graph illustrating time-domain waveforms measured by an exemplary GaSe terahertz frequency wave detector according to the present invention.
Figure 4B:
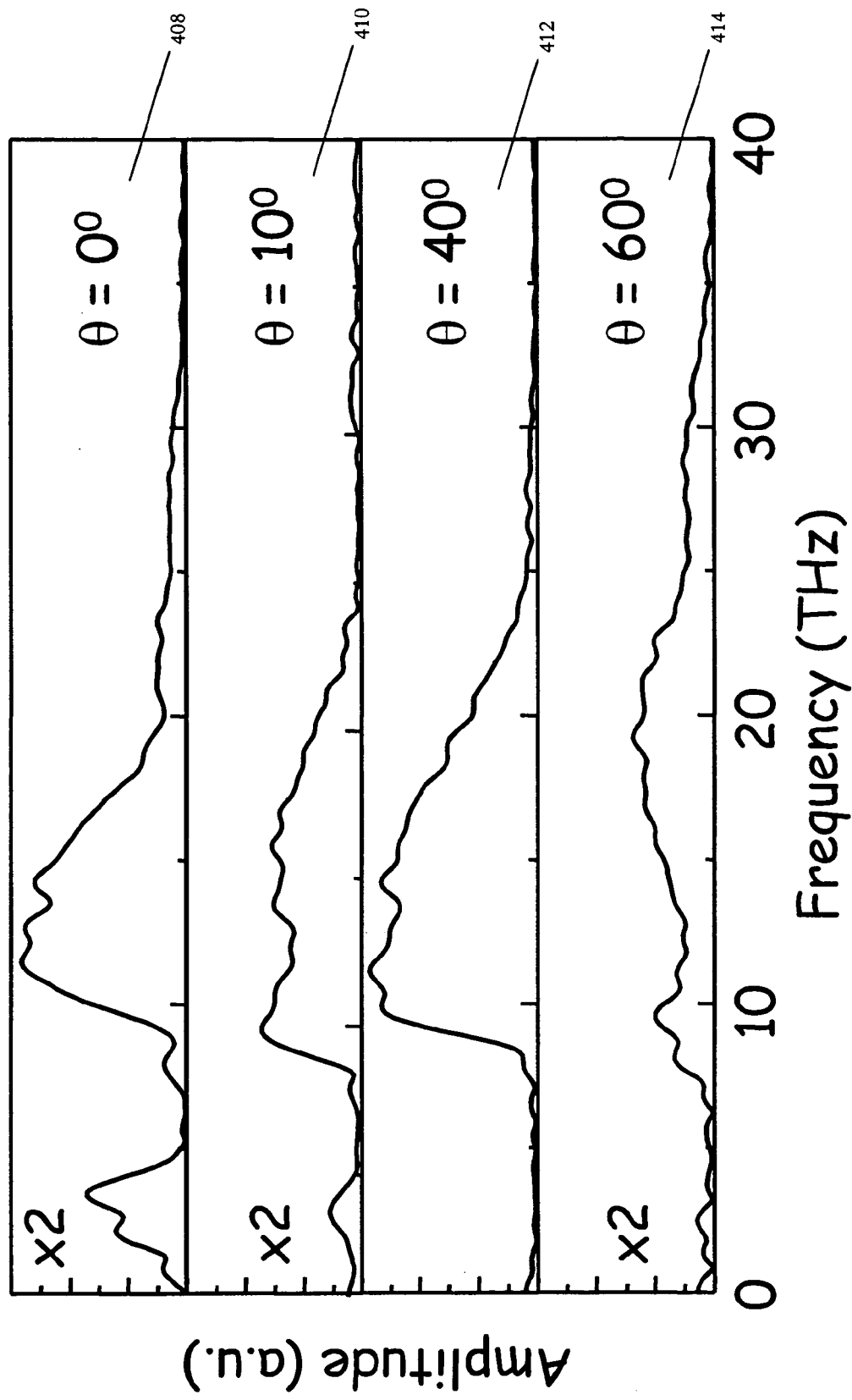
FIG. 4B is a graph illustrating frequency-domain spectra measured by an exemplary GaSe terahertz frequency wave detector according to the present invention.

The intensity information of the THz frequency pulses determined by the calculation means may desirably include: time-domain waveforms, as shown in graph 300 of FIG. 3 and graphs 400, 402, 404, and 406 of FIG. 4A; or frequency-domain spectra, as shown in graph 302 of FIG. 3 and graphs 408, 410, 412, and 414 of FIG. 4B. Time-domain waveforms may be obtained directly from the variations of the probe polarization. Frequency-domain spectra may be obtained from the time-domain waveforms by a Fourier transform. The calculation means may use a number of detector parameters to scale the intensity information of the THz frequency pulses from the intensity values corresponding to the varying probe polarization. These parameters may include phase-matching angle 118, the interaction thickness of GaSe substrate 116, the initial polarization state of the probe optical beam, and, if the probe optical beam is linearly polarized, the polarization angle between the polarization axis of the probe optical beam and the optical axis of GaSe substrate 116.

Desirably, the bandwidth of the intensity information of the THz frequency pulses determined by the calculation means is greater than about 20 THz and may exceed 100 THz. One exemplary method to increase the bandwidth is to calculate a weighted average of a number of measurements while one, or more, detector parameters are varied. Additionally, the quality of the intensity information may be improved by averaging measurements for a number of THz pulses measured using the same parameters.

Both phase-matching angle 118 and the interaction thickness may affect the central frequency and the spectral composition of the detected signal as well. Experimental results, described in detail below, demonstrate the effect of the interaction thickness of GaSe substrate 116 on the spectral response and sensitivity of an exemplary broad bandwidth detector, such as that illustrated in FIG. 1. These results indicate that as the interaction thickness increases the sensitivity of the exemplary broad bandwidth detector increases, up to a critical thickness after which the sensitivity remains substantially constant. Additionally, these results indicate that as the interaction thickness decreases the bandwidth of the exemplary broad bandwidth detector increases, down to approximately the critical thickness after which the bandwidth remains substantially constant. The critical thickness may depend on a number of other parameters of the broad bandwidth detector, such as the probe peak wavelength, the probe pulse width, and the THz pulse width. Therefore, although it is contemplated that interaction thickness may be selected over a relatively broad range about 20 µm to about 100 µm, it may be desirable for the interaction thickness to be in a narrower range near the critical thickness. For the exemplary system described below reference to FIGS. 3 and 4A and 4B, the critical thickness may be in the range of about 35 µm to about 40 µm.

FIG. 4B illustrates exemplary effects of phase-matching angle 118 on the central frequency and the spectral composition of the detected signal. Unlike the interaction thickness of GaSe substrate 116, phase-matching angle 118 may be relatively easily varied during the measurement of a number of THz frequency pulses. An exemplary broad bandwidth detector may include a controllable θ rotation stage (not shown) coupled to GaSe substrate to controllably vary phase-matching angle 118. This controllable θ rotation stage may allow a detection spectral envelope of the broad bandwidth detector to be controllably varied.

In one exemplary embodiment, the controllable θ rotation stage may be used to sweep phase-matching angle 118 through a phase-matching angle range, which may extend from about −80° to about 80°, as a set of THz frequency pulses are coupled into GaSe substrate 116. Desirably, the phase-matching angle for each pulse of a set of THz frequency pulses is stepped by an equal angle. Because the THz frequency pulses of this set of THz frequency pulses each intersect GaSe substrate 116 at a different phase-matching angle, the probe polarizations of the probe optical beam corresponding to each THz frequency pulse may vary differently. The probe polarizations of the probe optical beam corresponding to the set of THz frequency pulses may desirably be analyzed separately by the calculation means to determine individual intensity information corresponding to each pulse of the set of THz pulses. This individual intensity information may then be combined, desirably in frequency space, to determine averaged intensity information corresponding to the set of THz frequency pulses, with a broader bandwidth than the intensity information from measurements using only one phase-matching angle.

The controllable θ rotation stage may also include an angular position sensor (not shown) calibrated to determine phase-matching angle 118. This angular position sensor may desirably be electrically coupled to the calculation means, which may use the determined phase-matching angle as well as the detected probe polarization to determine the intensity information.

In another exemplary embodiment, a controllable φ rotation stage (not shown) may be coupled to the GaSe substrate to controllably rotate the GaSe substrate around normal 120 of the front surface of the GaSe substrate, thereby varying a polarization angle of the probe optical beam relative to the optical axis of the GaSe substrate. By varying the polarization angle of the probe optical beam relative to the optical axis of the GaSe substrate, the detection spectral envelope of the broad bandwidth detector may be controllably varied. The controllable φ rotation stage may include an angular position sensor calibrated to determine a polarization angle of the probe optical beam relative to the optical axis of the GaSe substrate and provide this information to the calculation means.

Alternatively, the coupling optics include controllable polarization rotator 108, which may be a mechanical or an electro-optically controlled polarization rotator. Controllable polarization rotator 108 may controllably rotate the probe polarization of the probe optical beam, thus varying a polarization angle of the probe optical beam relative to the optical axis of the GaSe substrate. Controllable polarization rotator 108 may include a polarization angle sensor calibrated to determine a polarization angle of the probe optical beam relative to the optical axis of the GaSe substrate and provide this information to the calculation means.

Similarly to the controllable θ rotation stage, controllable polarization rotator 108, or the controllable φ rotation stage, may be used to sweep polarization angle of the probe optical beam relative to the optical axis of the GaSe substrate through a polarization angle range (up to 90°) as a set of THz frequency pulses pass are coupled into GaSe substrate 116. Desirably, the polarization angle for each pulse of a set of THz frequency pulses is stepped by an equal angle. Because the THz frequency pulses of this set of THz frequency pulses each intersect GaSe substrate 116 at a different polarization angle, the probe polarizations of the probe optical beam corresponding to each THz frequency pulse may vary differently. The probe polarizations of the probe optical beam corresponding to the set of THz frequency pulses may desirably be analyzed separately by the calculation means to determine individual intensity information corresponding to each pulse of the set of THz pulses. This individual intensity information may then be combined, desirably in frequency space, to determine averaged intensity information corresponding to the set of THz frequency pulses, with a broader bandwidth than the intensity information from measurements using only one polarization angle.

In an exemplary embodiment in which the probe optical beam includes a plurality of probe pulses having probe pulse widths less than the THz pulse width of the THz frequency pulses, only a portion of each THz frequency pulses may be measured by the exemplary broad bandwidth detector. In this case, it may be desirable for optical delay line 104 of the coupling optics to be a variable optical delay line. This variable optical delay line may be used to change the portion of a corresponding one of the THz frequency pulses to which each probe pulse is synchronized such that the set of probe pulses are swept over a corresponding set of THz frequency pulses.

The probe pulses of this set of probe pulses each interact in GaSe substrate 116 with a different portion of a corresponding THz frequency pulse. The probe polarizations of each probe pulse may desirably be analyzed separately by the calculation means to determine individual intensity information corresponding to each pulse of the set of probe pulses. This individual intensity information may then be combined, desirably in temporal space, to determine averaged intensity information corresponding to the entire THz frequency pulse.

It is noted that other parameters of the broad bandwidth detector may be varied and the resulting sets of individual pulse intensity information combined by the calculation means as well. Also, two or more parameters may be varied creating multidimensional arrays of individual pulse intensity information that may be combined to further enhance the resulting averaged intensity information of the series of THz frequency pulses.

An experimental study of GaSe crystals as coherent broadband THz wave detectors has been performed using an exemplary broad bandwidth detector according to the present invention ("GaSe Crystals for Broadband Terahertz Wave Detection", K. Liu, J. Xu, and X.-C. Zhang, presented at Nonlinear Optics: Materials, Fundamentals and Applications, MC7, Hawaii Island, Hi., Aug. 2, 2004). These experimental results indicate that GaSe may provide a good sensor crystal for broadband THz waves with a sub-20 fs laser system. The sensitivity of the exemplary GaSe crystal exceeds that of a reference ZnTe crystal with a comparable detection bandwidth. Furthermore, the central frequency of THz pulses detected by the GaSe crystal may be varied by tilting the angle about the vertical axis which is perpendicular to the direction of the probe beam. This suggests that GaSe may be also used as a narrowband detector.

FIG. 3 shows time-domain waveform 300 and frequency-domain spectra 302 of THz waves detected using the GaSe (thicker line) crystal and the ZnTe (thinner line) crystal, respectively.

The optical source utilized in this experiment was a Ti:Sapphire laser with a 75-MHz repetition rate, 360 mW average power, 790 nm wavelength, 108 nm spectral bandwidth, and 10-fs pulse duration. THz radiation was generated and detected using a 43 μm GaSe crystal and a 37 μm GaSe crystal, as the emitter and sensor, respectively. Both were peeled off from the same piece of Z-cut as grown crystal without antireflection coatings. Two off-axis parabolic mirrors were used to collect, collimate, and refocus the THz wave. During the experiment, the sensor crystal was tilted by an angle, θ (phase matching angle), around the vertical axis perpendicular to the direction of the probe beam. For comparison, a 21 μm <110> oriented ZnTe crystal was used as a reference sensor.

The GaSe crystal is tilted 45° with respect to the incident beam; at this incident angle the detected THz wave peak field is about three times higher than that with normal incidence. As indicated in FIG. 3, the THz wave peak field amplitude detected with the GaSe is also three times larger than the largest THz peak signal measured with the reference ZnTe. The bandwidth of the THz wave detected by the GaSe crystal covers from 10 THz to more than 30 THz.

Difference in GaSe and ZnTe sensing performance could be attributed to their second order electro-optic coefficients: $r_{22}$(GaSe)=54 pm/V versus $r_{41}$(ZnTe)=4 pm/V, and velocity mismatching. GaSe has a large birefringence and consequently its phase matching condition can be achieved in a broad wavelength range. One skilled in the art may understand that a thin ZnTe crystal is required to support a broader detection bandwidth. To achieve the same bandwidth detected by a 37 μm GaSe crystal, a ZnTe crystal with the thickness less than 21 μm may need to be used. However, the sensitivity of detection with a thinner ZnTe crystal is greatly reduced due to the lack of interaction length.

Although the second order nonlinear coefficient of a GaSe crystal is almost thirteen times larger than that of ZnTe crystal, the measured sensitivity of the exemplary GaSe crystal THz wave detector is only three times larger than that of the ZnTe reference crystal THz wave detector. This is due to the velocity mismatch in the GaSe crystal resulting from the birefringence. An ultra-short pulse <20 fs propagates in a GaSe crystal with a spatial length <2 μm and has different propagation velocities in ordinary and extraordinary orientations. This difference in velocity separates the ordinary and extraordinary components after the pulse has propagated through the GaSe crystal a distance of about 20 μm. The nonlinear interaction gradually reduces during this process. Therefore, this condition decreases the efficient detection with a thick GaSe crystal. A direct proof is that the measurement with a GaSe crystal thicker than 40 μm did not have a significantly higher detection sensitivity. Similar phenomena have been reported in THz wave generation, where the same amplitude of THz radiation is generated using either a 140 μm GaSe crystal or a 90 μm GaSe crystal (W. Shi, Y. J. Ding, N. Fernelius, and K. Vodopyanov, Opt. Lett. 27, 1454 (2002)). When a nanosecond optical pulse is used in THz wave generation, the velocity mismatch may be neglected due to the long pulse duration. A 1.5 cm GaSe crystal may generate THz waves with 3.3% photon conversion efficiency (V. G. Dmitriev, G. G. Gurzadyhan, and D. N. Nikogosyan, Handbook of Nonlinear optical crystals, Springer, 166-169 (1999)) using a nanosecond laser pulse.

It had been reported (R. Huber, A. Brodschelm, F. Tauser, and A. Leitenstorfer, Appl. Phys. Lett. 76, 3191 (2000); K. Reimann, R. P. Smith, A. M. Weiner, T. Elsaesser, and M. Woerner, Opt. Lett. 28, 471 (2003); and R. A. Kaindl, D. C. Smith, M. Joschko, M. P. Hasselbeck, M. Woerner, and T. Elsaesser, Opt. Lett. 23, 861 (1998)) that the central frequency of THz pulses generated from GaSe crystals are tunable. The generated THz waves may tuned by varying the phase-matching angle, which substantially changes the phase-matching condition in the GaSe crystal. An exemplary THz wave sensor using a GaSe crystal may exhibit similar properties.

FIG. 4A illustrates time-domain THz waveforms 400, 402, 404, and 406 detected by the exemplary GaSe crystal THz wave sensor, with a phase matching angle of θ=0°, 20°, 40°, 60°, respectively. Both the THz electric field oscillation frequency and amplitude increase as the phase matching angle increases. At θ=40° the THz wave amplitude is about three times higher than the THz wave amplitude with θ=0°. Once θ>40°, field amplitude starts to decrease.

FIG. 4B illustrates the THz wave spectra 408, 410, 412, and 414 derived by Fourier transform from the corresponding time-domain THz waveforms 400, 402, 404, and 406 of FIG. 4A. A transverse optical phonon absorption band centers at 7.1 THz. Above this phonon region, the central frequency of the frequency-domain spectra increases when the tilted phase matching angle increases, corresponding to the higher oscillation in FIG. 4A. At θ=40°, the THz wave spectra between DC and the 8 THz region nearly disappears, but the frequency-domain spectra within 10 THz-40 THz becomes very prominent. At larger phase-matching angles the frequency-domain spectrum splits into two parts: one narrow peak around 10 THz and another broad frequency-domain spectrum with blue shift as the phase-matching angle increases.

The frequency-domain spectra evolution versus phase-matching angle in this exemplary GaSe sensor is similar to the experimental results of the GaSe emitter reported by Huber et al. (Appl. Phys. Lett. 76, 3191 (2000)). In Huber's experiment, the polarization of the pump beam is rotated 45° in order to provide both ordinary and extraordinary polarized components in the optical beam to satisfy type-I phase-matching conditions for an ordinary polarized THz wave component. Different spectral components of the pump beam contribute to the phase-matching process, as well. By varying the phase-matching angle, the central frequency of the output THz wave may be tuned. This observation can be generally described by the phase-matching equation:

$$\Delta k(\omega, \Delta\omega, \theta) = [n_e(\omega + \Delta\omega, \theta) \cdot (\omega + \Delta\omega) - n_o(\omega) \cdot \omega - n_0(\Delta\omega) \cdot \Delta\omega]/c \quad (1).$$

Here $n_0$ and $n_e$ are the frequency dependent ordinary and extraordinary refractive index, respectively. In contrast to the generation case, where the polarization of the pump beam is rotated 45° for phase matching, the probe beam maintains a horizontal polarization in this exemplary experiment. The ordinary polarization component is generated in a second order nonlinear process between the probe beam and THz radiation. As a result, the detection process follows the same phase match rule as the generation. The angular-dependent extraordinary refractive index:

$$n_e(\theta) = n_0 \sqrt{(1 + \tan^2\theta)/(1 + n_0^2 \tan^2\theta / n_e^2)} \; ; \quad (2)$$

decreases with increasing the phase-matching angle θ in a negative uniaxial crystal. The phase matching condition can also be described as:

$$(n_o - n_e(\theta))/(n_e(\theta) - n_T) = \Delta\omega/\omega \quad (3).$$

From these equations, one skilled in the art may understand that the phase matched THz wave frequency desirably increases as the phase-matching angle increases. Thus, the evolution of THz spectra resulting from tuning the phase-matching angle is similar for GaSe emitters and sensors.

Although illustrated and described above with reference to certain specific embodiments, the present invention is nevertheless not intended to be limited to the details shown. Rather, various modifications may be made in the details within the scope and range of equivalents of the claims and without departing from the invention.

What is claimed is:

1. A broad bandwidth detector for use with a coherent optical source to measure intensity information of terahertz (THz) frequency pulses which have a THz pulse period, each THz pulse having a THz pulse width, the broad bandwidth detector comprising:
   coupling optics optically coupled to the coherent optical source to direct a probe optical beam produced by the coherent optical source along a probe beam path substantially collinear with a pulse beam path of the THz frequency pulses;
   a GaSe substrate having a first surface and a second surface substantially parallel to the first surface, the GaSe aligned such that the probe beam path intersects the first surface at a phase-matching angle and a probe polarization of the probe optical beam is varied based on interactions between the probe optical beam and the THz frequency pulses within the GaSe substrate;
   a polarization detector aligned in the probe beam path to detect the varied probe polarization of the probe optical beam; and
   calculation means electrically coupled to the polarization detector to determine the intensity information of the THz frequency pulses based on the detected probe polarization of the probe optical beam.

2. A broad bandwidth detector according to claim 1, wherein:
   the coherent optical source is a pulsed coherent optical source; and
   the probe optical beam comprises a plurality of probe pulses; and
   the plurality of probe pulses have a probe pulse period substantially equal to the THz pulse period of the THz frequency pulses.

3. A broad bandwidth detector according to claim 2, wherein: each THz pulse has a THz pulse width; and
   each probe pulse has a probe pulse width less than the THz pulse width of the THz frequency pulses.

4. A broad bandwidth detector according to claim 3, wherein the coupling optics comprise an optical delay line to synchronize each probe pulse to a portion of a corresponding one of the THz frequency pulses.

5. A broad bandwidth detector according to claim 4, wherein:
   the optical delay line is a variable optical delay line to change the portion of the corresponding one of the THz frequency pulses synchronized to each probe pulse in a set of probe pulses such that the set of probe pulses are swept over a corresponding set of THz frequency pulses; and
   the calculation means is adapted to determine the intensity information based on the detected probe polarizations of the set of probe pulses.

6. A broad bandwidth detector according to claim 4, wherein the optical delay line is aligned to delay one of:
   the plurality of probe pulses; or
   the plurality of THz frequency pulses.

7. A broad bandwidth detector according to claim 2, wherein the coherent optical source is a Ti:Sapphire ultrafast laser.

8. A broad bandwidth detector according to claim 2, wherein the probe pulse width of the plurality of probe pulses is less than or equal to about 100 fs.

9. A broad bandwidth detector according to claim 1, wherein a probe peak wavelength of the probe optical beam is less than or equal to about 1 μm.

10. A broad bandwidth detector according to claim 1, wherein the Gase substrate is controllably rotatable about a θ axis to vary the phase-matching angle, so that a detection spectral envelope of the broad bandwidth detector is controllably varied.

11. A broad bandwidth detector according to claim 10, wherein:
    the Gase substrate is controllably rotated to sweep the phase-matching angle of a set of THz frequency pulses through a phase-matching angle range in substantially equal angular steps; and
    the calculation means is adapted to determine the intensity information based on the detected probe polarizations of the probe optical beam corresponding to the set of THz frequency pulses.

12. A broad bandwidth detector according to claim 10, wherein the calculation means is adapted to determine the intensity information based on the detected probe polarization and the phase-matching angle.

13. A broad bandwidth detector for use with a coherent optical source to measure intensity information of terahertz (THz) frequency pulses which have a THz pulse period, each THz pulse having a THz pulse width, the broad bandwidth detector comprising:
    coupling optics optically coupled to the coherent optical source to direct a probe optical beam produced by the coherent optical source along a probe beam path substantially collinear with a pulse beam path of the THz frequency pulses;
    a GaSe substrate having a first surface and a second surface substantially parallel to the first surface, the GaSe aligned such that the probe beam oath intersects the first surface at a phase-matching angle and a probe polarization of the probe optical beam is varied based on interactions between the probe optical beam and the THz frequency pulses within the GaSe substrate;
    a polarization detector aligned in the probe beam path to detect the varied probe polarization of the probe optical beam; and
    calculation means electrically coupled to the polarization detector to determine the intensity information of the THz frequency pulses based on the detected probe polarization of the probe optical beam;
    wherein the GaSe substrate is controllably rotatable about a Φ axis around a normal of the first surface of the GaSe substrate to vary a polarization angle of the probe optical beam relative to an optical axis of the GaSe substrate, such that a detection spectral envelope of the broad bandwidth detector is controllably varied.

14. A broad bandwidth detector according to claim 13, wherein:
the Gase substrate is controllably rotated to sweep the polarization angle of the probe optical beam relative to the optical axis of the GaSe substrate through a polarization angle range during a set of THz frequency pulses; and
the calculation means is adapted to determine the intensity information based on the detected probe polarizations of the probe optical beam corresponding to the set of THz frequency pulses.

15. A broad bandwidth detector according to claim 13, wherein the calculation means is adapted to determine the intensity information based on the detected probe polarization and the polarization angle.

16. A broad bandwidth detector according to claim 1, wherein the coupling optics comprise a controllable polarization rotator optically coupled to the coherent optical source to controllably rotate the probe polarization of the probe optical beam, for varying a polarization angle of the probe optical beam relative to an optical axis of the GaSe substrate, such that a detection spectral envelope of the broad bandwidth detector is controllably varied.

17. A broad bandwidth detector according to claim 16, wherein:
the controllable polarization rotator sweeps the polarization angle of the probe optical beam relative to the optical axis of the Gase substrate through a polarization angle range during a set of THz frequency pulses; and
the calculation means is adapted to determine the intensity information based on the detected probe polarizations of the probe optical beam corresponding to the set of THz frequency pulses.

18. A broad bandwidth detector according to claim 16, wherein:
the controllable polarization rotator comprises a polarization angle sensor electrically coupled to the calculation means;
the polarization angle sensor is calibrated to determine the polarization angle of the probe optical beam relative to the optical axis of the GaSe substrate; and
the calculation means is adapted to determine the intensity information based on the detected probe polarization and the determined polarization angle.

19. A broad bandwidth detector according to claim 1, wherein:
the first surface and the second surface separated by an interaction thickness; and
the interaction thickness of the GaSe substrate is in of range of about 20 μm to about 100 μm.

20. A broad bandwidth detector according to claim 1, wherein the polarization detector is adapted to detect an intensity of at least one polarization component of the probe optical beam.

21. A broad bandwidth detector according to claim 1, wherein the calculation means comprises at least one of special purpose circuitry, an ASIC, a digital signal processor, or a general purpose computer.

22. A broad bandwidth detector according to claim 1, wherein the intensity information of the THz frequency pulses determined by the calculation means comprises at least one of a time-domain waveform or a frequency-domain spectrum.

23. A broad bandwidth detector according to claim 1, wherein the intensity information of the THz frequency pulses determined by the calculation means has a bandwidth of greater than about 20 THz.

* * * * *